(12) United States Patent
Xiong

(10) Patent No.: US 8,076,156 B1
(45) Date of Patent: Dec. 13, 2011

(54) ISOTOPIC SIGNATURE CARBON TRACING METHOD TO DISCERN SHELLFISH-BASED GLUCOSAMINE FROM CORN-BASED GLUCOSAMINE

(75) Inventor: Lora Xiong, San Jose, CA (US)

(73) Assignee: Ethical Naturals, Inc., San Anselmo, CA (US)

( * ) Notice: Subject to any disclaimer, the term of this patent is extended or adjusted under 35 U.S.C. 154(b) by 7 days.

(21) Appl. No.: 12/455,231

(22) Filed: May 29, 2009

Related U.S. Application Data

(60) Provisional application No. 61/130,447, filed on May 30, 2008.

(51) Int. Cl.
*G01N 24/00* (2006.01)

(52) U.S. Cl. ............................. 436/173; 436/86; 436/87

(58) Field of Classification Search .......................... None
See application file for complete search history.

(56) References Cited

OTHER PUBLICATIONS

Tripp et al. "Single-Compound Isotopic Analysis of Organic Materials in Archaeology", LC•GC Europe, 2004, v. 17, No. 6, pp. 358-364.*

Webb et al. "Diet Quality Influences the δ13C and δ15N of locusts and their biochemical components", The Journal of Experimental Biology, 1998, v. 201, pp. 2903-2911.*

McConnaughey et al. "Carbon isotopes in mollusk shell carbonates", Geo-Mar Lett, 2008, 28, pp. 287-299.*

Haines "Relation between the stable carbon isotope composition of fiddler crabs, plants, and soils in a salt marsh", http://www.aslo.org/lo/toc/vol_21/issue_6/0880.pdf, 1976, v. 21, issue 6, pp. 880-884.*

* cited by examiner

*Primary Examiner* — Yelena G Gakh

(57) ABSTRACT

A glucosamine sample is analyzed using an isotope ratio mass spectrometer to determine whether the glucosamine sample is corn-based, e.g., vegetable-based, as opposed to shellfish-based. The isotope ratio mass spectrometer yields an isotopic value for $\delta^{13}C$ that is compared to a reference isotope value for corn, typically about −12.0%. If there is substantial agreement between the two ratios, then it is known with reasonable certainty that the glucosamine origin is corn and is thus vegetable-based. If there is substantial disagreement between the two ratios, it is known that the glucosamine is not corn-based and is likely shellfish-based. In this fashion, end consumers who cannot consume shellfish-based glucosamine, for reasons of religion or allergy, can purchase glucosamine with greater confidence.

2 Claims, 1 Drawing Sheet

ISOTOPIC SIGNATURE CARBON TRACING METHOD TO DISCERN SHELLFISH-BASED GLUCOSAMINE FROM CORN-BASED GLUCOSAMINE

RELATION TO CO-PENDING APPLICATION

Priority is claimed from co-pending U.S. provisional patent application Ser. No. 61/130,447, filed 30 May 2008, entitled Isotropic Signature Carbon Tracing Method to Discern Shellfish-Based Glucosamine From Vegetable-Based Glucosamine, and assigned to assignee herein.

FIELD OF THE INVENTION

The present invention relates generally to testing glucosamine samples, and more particularly to determining whether a sample of glucosamine was produced from from corn material, and is thus vegetable-based, rather than shellfish-based.

BACKGROUND OF THE INVENTION

The compound glucosamine comprises glucose and the amino acid glutamine and is found naturally in the human body, made from. Within the body, glucosamine helps produce glycosaminoglycan, a molecule used in the formation and repair of cartilage and other body tissues. Unfortunately as humans grow older the natural production of glucosamine tends to slow with the result that the movement of joints can become extremely painful. In diseases such as osteoarthritis the cartilage that normally cushions the joints can become stiff and non-elastic. As a result, movement of the joint, especially the knee, is not only very painful. If the body cannot produce adequate amounts of glucosamine to help repair the injury, the pain persists and the underlying problem is exacerbated as the joint continues to deteriorate with further movement.

It is known in the art to prescribe glucosamine as a food supplement to persons who suffer from joint pain associated with the body's inability to produce sufficient glucosamine. There is clinical evidence to suggest that taking glucosamine as a nutritional supplement can help repair damaged cartilage by augmenting the body's supply of glucosamine.

Glucosamine is commonly produced from either vegetable matter, e.g., corn, or from the shells of shellfish. Glucosamine is typically mass produced in powder form, with the powder having the same appearance, color, taste, and density, regardless of whether the glucosamine is vegetable-based or shellfish-based. The powder can be ingested with foods, mixed with liquids, or otherwise ingested. However, as a practical matter, neither the end consumer nor any intermediate producer can tell from looking at the glucosamine powder whether it was produced from vegetable matter or from shells from shellfish.

While the source of their glucosamine powder may be of no interest to many consumers, to other consumers it is critical to know whether the glucosamine is vegetable-based or shellfish-based. For some consumers, religious tradition may forbid the ingestion of shellfish based foodstuff. For other consumers who may be allergic to shellfish, ingesting glucose made from shellfish material can cause sickness or even death. Thus, in many instances, a consumer's ingesting shellfish-based glucosamine inadvertently marked by the manufacturer or an intermediate producer as being vegetable-based can have grave consequences.

Thus there is a need for a method by which a manufacturer or intermediate producer of glucosamine can confirm with certainty whether a glucosamine sample under test is vegetable-based or shellfish-based. In this manner, an end consumer purchasing glucosamine marked as vegetable-based can know with certainty that he or she will not be ingesting shellfish material.

The present invention provides such a method.

SUMMARY OF THE INVENTION

A sample of glucosamine is examined using an isotope ratio mass spectrometer to determine whether the glucosamine sample is vegetable-based as opposed to shellfish-based. The isotope ratio mass spectrometer yields an isotopic value for $^{13}C$ isotopes that is compared to a reference isotope value for corn, typically about −12.0%. If there is substantial agreement between the two ratios, then it is known with reasonable certainty that the glucosamine origin is corn and is thus vegetable-based glucosamine. But if there is substantial disagreement between the two ratios, it is known that the glucosamine is not from corn and most probably is shellfish-based glucosamine. In this fashion, end consumers who cannot consume shellfish-based glucosamine, for reasons of religion, allergy, etc., can purchase glucosamine with greater confidence. In a preferred embodiment, the sample is also compared to a reference isotope value for shellfish. If there is substantial agreement between the sample and the shellfish reference, then the sample is more definitely known to be shellfish based but not vegetable-based. This double-sampling provides a measure of security that is important in ensuring that a product labeled as vegetable-based is indeed vegetable-based and not shellfish-based.

Other features and advantages of the invention will appear from the following description in which the preferred embodiments have been set forth in detail, in conjunction with the accompany drawings.

DETAILED DESCRIPTION OF THE PREFERRED EMBODIMENTS

Figure 1:
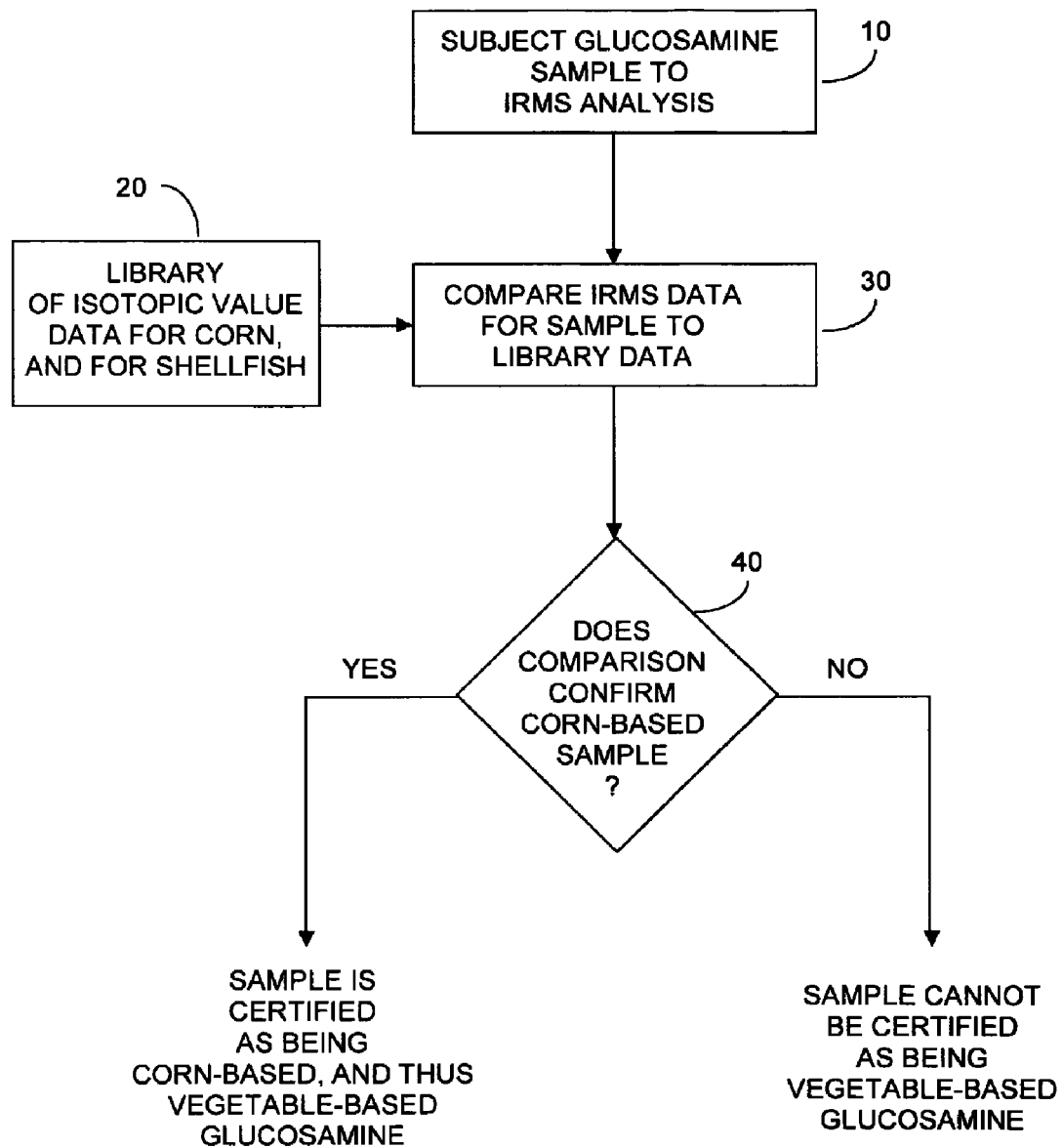
FIG. 1 depicts an exemplary method for testing samples of glucosamine to determine whether they were produced from vegetable matter, more specifically from corn, or were produced from shellfish, according to the present invention.

The present invention examines the isotopic signature of glucosamine samples to determine whether the glucosamine was produced from corn (e.g., from vegetable matter) or from shellfish (e.g., non-vegetable matter). An isotopic signature (or isotopic fingerprint) of a sample is a ratio of stable or unstable isotopes of particular elements found in the sample under test. The term isotope refers to one or more atoms that have the same atomic number but have different numbers of neutrons. The atomic mass of different isotopes affects their chemical kinetic behavior, leading to natural isotope separation processes.

It is common to examine carbon traces in the sample under test, using isotopic measurements. Isotopes of carbon are atomic nuclei that contain six protons plus 2 to 16 neutrons. Carbon has two stable naturally occurring isotopes. The isotope carbon-12 ($^{12}C$) forms 98.93% of the carbon on earth and has an atomic mass of about 13, while carbon-13 ($^{13}C$) forms the remaining 1.07% and has an atomic mass of about 12. The concentration of $^{12}C$ is further increased in biological materials because biochemical reactions discriminate against $^{13}C$.

Isotopic measurements are often expressed in so-called delta notation. When carbon is the element of interest, the $\delta\ ^{13}C$ value (pronounced "delta C 13") is observed. $\delta\ ^{13}C$ values are expressed as a per mil (‰) deviation, e.g., per one thousand, from an internationally accepted PDB standard (a carbonate from the Pee Dee Belemnite formation in South Carolina). $\delta\ ^{13}C$ values are determined using the following formula:

$$\delta^{13}C = \frac{(\delta^{13}C/\delta^{12}C)_{sample} - (\delta^{13}C/\delta^{12}C)_{PDB}}{(\delta^{13}C/\delta^{12}C)_{PDB}} \times 1000$$

where PDB=Pee Dee Belemnite, a carbonate from the Pee Dee formation in South Carolina.

The naturally occurring $\delta\ ^{13}C$ values for biologically interesting carbon compounds range from roughly 0‰ to −110‰ relative to the PDB standard. Variations are often a result of different photosynthetic pathways or usage of the distinguish isotopes in chemical reactions.

When atmospheric $CO_2$ is converted to a phosphoglycerate compound with three C atoms, C3 plants show $\delta\ ^{13}C$ ranging from −32‰ to −20‰. C3 plants include rice, wheat, soybeans, and potatoes. On the other hand, if atmospheric $CO_2$ is converted to dicarboxylic acid with four C atoms, C4 plants have higher $\delta\ ^{13}C$ values ranging from −17‰ to −9‰. C4 plants include corn, maize, and corn-fed beef and are characteristically found in hot, arid environments. The different percentages for C3 and C4 plants occur because the isotope separation effect is more pronounced in C3 carbon fixation, while the heavier $^{13}C$ is less depleted in C4 carbon fixation.

The different isotope ratios for the two kinds of plants, C3 and C4, propagate through the food chain. As a result, it is possible using isotope analysis of flesh and bone collagen to determine whether the principal diet of a human or an animal consists primarily of C3 plants or C4 plants. C4 plants. In similar fashion, other chemical reactions create isotopic differences when comparing products to reactants, and can provide an isotopic signature or fingerprint that can differentiate two otherwise identical compounds. Relative to the present invention, the two otherwise identical compounds to be differentiated are vegetable-based glucosamine and shellfish-based glucosamine.

Stable isotope ratio mass spectrometry has been used to identify isotopic signatures of materials in the field of forensics. For example, oil within an oil spill on the ocean can be examined using isotope ratio mass spectrometry to discern the origin of the oil, and thus perhaps identify the party liable for the cost of cleaning up the oil spill. In the field of agriculture, isotope signatures of plants can to some degree be influenced by the plant growing conditions, including moisture and nutrient availability. In the field of synthetic materials, isotopic signatures are influenced by conditions during the chemical reaction.

Isotopic signature profiling is especially useful where other types of profiling, e.g. characterization of impurities, are not optimal. For example, different sources and sinks of methane have different affinity for the $^{12}C$ and $^{13}C$ isotopes. Advantageously this allows distinguishing between different sources by examining the $^{13}C/^{12}C$ ratio in methane in the air.

With respect to the present invention, USP grade glucosamines resulting from corn fermentation or shellfish are each highly purified products, e.g., at least 99% purity, that have very similar physical and chemical characteristics. As such, using common test methods it is difficult to examine a sample of glucosamine and determine whether it is corn-based, e.g., vegetable-based or shellfish-based. As noted earlier herein, an incorrect determination as to the source material in glucosamine can sometimes have very bad effects to the consumer.

However tests by applicants have demonstrated that due to the special photosynthesis pathway of maize and corn, the isotopic figure-print test of $\delta\ ^{13}C$ provides a reliable and unique way to identify the vegetable-based glucosamine. As shown by FIG. 1, at method step 10, a sample of glucosamine whose vegetable-vs.-shellfish origin is to be determined, is examined with an isotope ratio mass spectrometer (IRMS). The details associated with conducting an analysis using an IRMS are known in the art and thus need not be described here.

As noted by step 20, there will previously be stored and made available for use during IRMS sample analysis, a library including isotopic data values representing corn and representing shellfish, e.g., the two common source materials for glucosamine.

At step 30, the analysis results from step 10 for the glucosamine sample under test are compared, preferably first against the library-stored data for corn and then against the library-stored data for shellfish. At step 40, if the results from step 30 agree within an acceptable degree of certitude with the data stored in the library at step 20 for corn, e.g., an isotopic value of about −12.0‰, then very likely the sample under test is glucosamine. However it is preferred that the step 40 analysis results for the glucosamine sample under test are also compared with the library-stored value for shellfish. If the results from step 40 are acceptably close to the step 10 library-stored reference data for corn and substantially different from the library reference data for shellfish, then the sample under test can safely and reliably be certified as being corn-based, i.e., vegetable-based, and not shellfish based. But if step 30 indicates otherwise, then the sample under test cannot and should not be certified as being vegetable-based. This latter statement is explicitly true if the comparison result at step 40 confirms a shellfish-based sample.

In short, the present invention provides a straightforward go, no-go method of certifying that glucosamine has been produced from corn-based material, e.g., from vegetable-based material, and not from shellfish-based material. As noted, the consumption of shellfish-based glucosamine by a person expecting the glucosamine to be vegetable-based can have dire results if the person is allergic to shellfish, or for religious reasons is proscribed from consuming shellfish.

Modifications and variations may be made to the disclosed embodiments without departing from the subject and spirit of the present invention as defined by the following claims.

What is claimed is:

1. A method to determine from a sample of glucosamine whether the glucosamine is corn-based or shellfish-based, the method comprising the following steps:
   (a) examining said sample using an isotope ratio mass spectrometer;
   (b) determining for said sample examined at step (a) an isotopic $\delta\ ^{13}C$ value;
   (c) if the isotopic $\delta\ ^{13}C$ value of the sample is close to approximately −12‰, the reference isotopic $\delta\ ^{13}C$ value for corn, certifying that the sample is corn-based;
   if the isotopic $\delta\ ^{13}C$ value of the sample is close to approximately −22‰, the reference isotopic $\delta\ ^{13}C$ value for shellfish, certifying that the sample is shellfish-based.

2. The method of claim 1, wherein:
   in step (c) if the isotopic $\delta\ ^{13}C$ value of the sample is neither close to approximately −12‰, nor close to approximately −22‰, not certifying the sample as corn-based or shellfish-based.

* * * * *